United States Patent [19]

Zaby et al.

[11] Patent Number: 5,117,048

[45] Date of Patent: May 26, 1992

[54] PROCESS FOR THE CONTINUOUS PREPARATION OF MONOISOCYANATES OR POLYISOCYANATES

[75] Inventors: Gottfried Zaby, Leverkusen; Helmut Judat, Langenfeld, both of Fed. Rep. of Germany; Eric Boonstra, Oakdale, Pa.; Stefaan de Vos, Vaartlaan, Belgium; Rolf-W. Eckermann, Bergisch-Gladbach; Siegbert Humburger, Leverkusen, both of Fed. Rep. of Germany

[73] Assignee: Bayer Aktiengesellschaft, Leverkusen, Fed. Rep. of Germany

[21] Appl. No.: 284,204

[22] Filed: Dec. 14, 1988

[30] Foreign Application Priority Data

Dec. 24, 1987 [DE] Fed. Rep. of Germany ........ 3744001

[51] Int. Cl.⁵ ............................................ C07C 249/00
[52] U.S. Cl. ................................................... 560/347
[58] Field of Search ........................................ 560/347

[56] References Cited

U.S. PATENT DOCUMENTS

| | | |
|---|---|---|
| 3,226,410 | 12/1965 | Hettich et al. . |
| 3,507,626 | 4/1970 | Horn ..................................... 23/284 |
| 3,947,484 | 3/1976 | Mitrowsky et al. . |
| 4,289,732 | 9/1981 | Bauer et al. ........................ 560/347 |

FOREIGN PATENT DOCUMENTS

| | | | |
|---|---|---|---|
| 1238669 | 7/1971 | United Kingdom ................ 560/347 |
| 2036586 | 7/1980 | United Kingdom . |

*Primary Examiner*—Alan Siegel
*Attorney, Agent, or Firm*—Joseph C. Gil; Richard E. L. Henderson

[57] ABSTRACT

The present invention relates to a process for the continuous preparation of organic mono- or polyisocyanates by the reaction of the mono- or polyamines corresponding to the mono- or polyisocyanates with phosgene dissolved in an organic solvent. The phosgene solution and the amine component, optionally also in the form of a solution, are brought together inside a nozzle (1) by subjecting the stream of one component to a constriction (3) and supplying the other component into this constriction (3) from the side as partial streams through several apertures (5).

20 Claims, 1 Drawing Sheet

PROCESS FOR THE CONTINUOUS PREPARATION OF MONOISOCYANATES OR POLYISOCYANATES

BACKGROUND OF THE INVENTION

This invention relates to a process for the continuous preparation of organic mono- or polyisocyanates by the reaction of mono- or polyamines corresponding to the mono- or polyisocyanates with a solution of phosgene in organic solvents at elevated temperatures.

It is known to prepare reaction mixtures of organic amine solutions and organic phosgene solutions in mixers with movable parts, such as rotary pump mixers. E.g., DE-AS 2,153,268 or U.S. Pat. No. 3,947,484. Due to the toxicity of phosgene, leakage at the points where the shafts pass through the apparatus can be particularly hazardous. Moreover, since the reaction also produces solids, the formation of deposits that cake to the surface of the apparatus may be unavoidable.

As a result, attempts have been made to find processes by which mixing can be carried out without moving parts. Thus, according to DE-OS 2,950,216, the two reactants impinge on each other in the form of fans of jet sprays in a cylindrical mixing chamber. Not only does this process require high inlet pressures, but blockages may also occur because of the dead zones of the mixing chamber where no flow takes place.

It is also known (e.g., U.S. Pat. No. 3,226,410) that the amine solution can be injected into a stream of phosgene solution in a pipe by means of apertures arranged laterally in the pipe. Since a low concentration of reactant is required for producing acceptable yields, the quantity of isocyanate produced is also small in proportion to the quantity of solvent. The large amount of energy consumption required for solvent recovery is an unsatisfactory aspect of the process. Moreover, build-up of layers of solids on the wall cannot always be avoided.

Since the known processes must be carried out with highly diluted reactants and since the frequent blockages force long periods of standstill for cleaning the apparatus, the known processes are uneconomical.

Thus, a new process for the continuous preparation of organic mono- or polyisocyanates in which the quantity of auxiliary solvent used could be considerably reduced while avoiding difficulties arising from the formation of solid deposits on the apparatus (and resultant blockages) would be desirable. Also desirable would be a new process that would dispense with the use of moving parts, thereby eliminating the above-mentioned hazards due to toxicity. The present invention provides a solution to these problems. In the process of this invention, the reaction mixture is prepared by bringing together the amine component, optionally as a solution, with the phosgene solution in a special nozzle of the type described hereinafter.

SUMMARY OF THE INVENTION

This invention relates to a process for the continuous preparation of organic mono- or polyisocyanates by the reaction of mono- or polyamines corresponding to the mono- or polyisocyanates with a solution of phosgene in suitable organic solvents at elevated temperatures, followed by distillative work-up of the resulting reaction mixture. To prepare the starting mixtures, the amine component (optionally dissolved in a substantially inert solvent) and the phosgene components are brought together in a nozzle (1) by confining by a constriction (3) an axial stream of one of the two components in this nozzle (1) and supplying the other component to the stream of first component in this constriction (3) as several partial lateral streams introduced from the side through a corresponding number of lateral bores (5) distributed over the circumference of the constriction (3).

BRIEF DESCRIPTION OF THE DRAWINGS

The drawings serve to illustrate in more detail the mixing apparatus which is essential for this invention.

Figure 1:
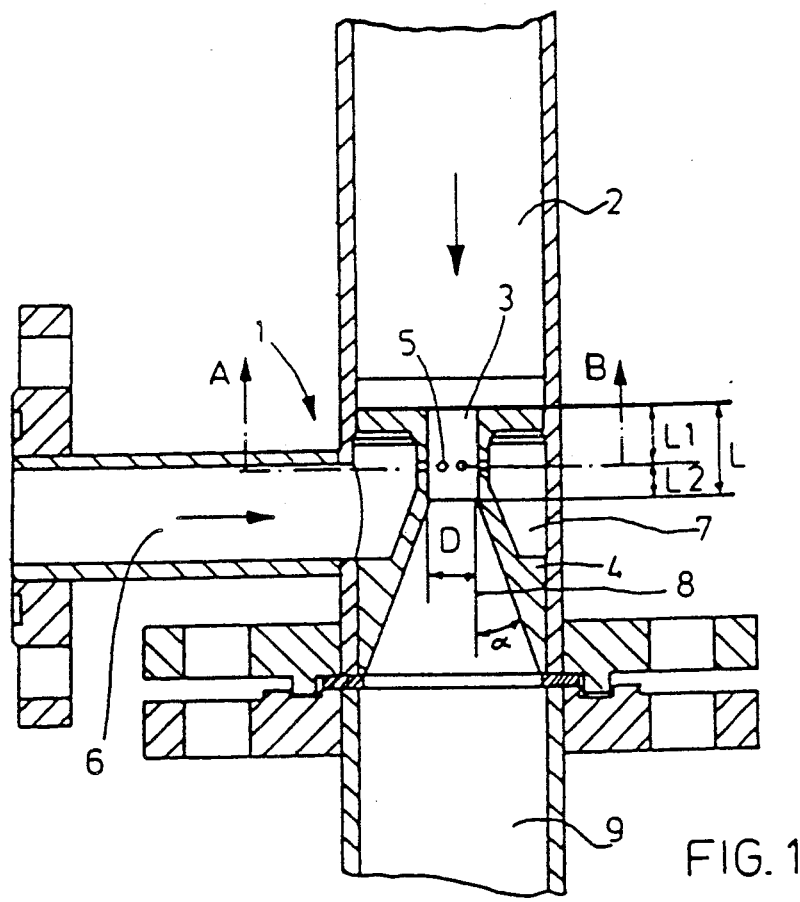
FIG. 1 shows the nozzle in longitudinal section.
Figure 2:
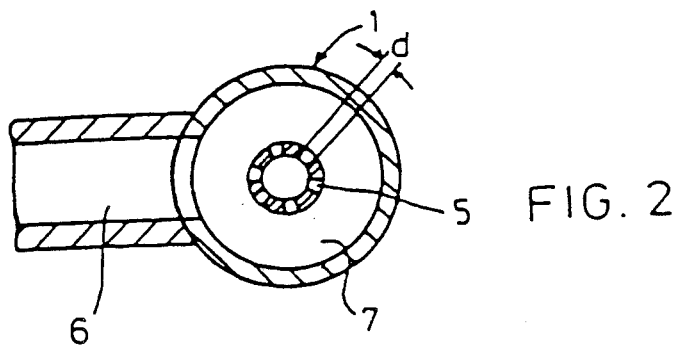
FIG. 2 is a section taken on the line A-B of FIG. 1.
Figure 3:
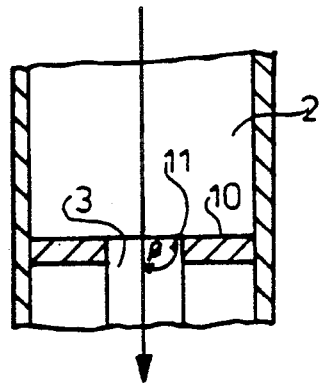
FIG. 3 shows the transition of the feed pipe into the constriction.

The various reference numerals have the following meaning:

(1) the nozzle to be used according to the invention;
(2) the feed pipe for the main stream;
(3) the sudden constriction of the main stream;
(4) the insert which produces the constriction, and the lateral bores formed in the insert;
(5) the lateral bores;
(6) the feed pipe introducing the lateral streams;
(7) the chamber which surrounds the constriction (3) and from which the bores (5) lead off;
(8) the portion of continuously increasing width at the outlet end of the nozzle;
(9) the discharge pipe;
(10) the barrier surface at the end of the feed pipe (2);
(11) the cut-off edge at the beginning of the constriction (3);

D the internal diameter of the constriction;
d the diameter of each lateral bore;
L the total length of the constriction;
$L_1$ the distance from the beginning of the constriction to the plane of the lateral bores; and
$L_2$ the distance from the plane of the lateral bores to the beginning of the portion of increasing width.

DESCRIPTION OF THE INVENTION

It has surprisingly been found that the process of this invention can be carried out with low pressure drops and higher concentrations, can provide a high product yield with very short residence times in the reaction chambers downstream of the mixing apparatus, and can avoid blockages and solid deposits. The nozzle used is designated an annular perforated nozzle. The constriction on the stream of solution may take place suddenly or continuously but is preferably produced by an abrupt narrowing of the supply pipe. Since a pressure drop of about 2 bar in the annular nozzle is generally sufficient for optimum mixing, the inlet pressures in the streams of solution may generally also be kept low. This enables conventional pumps to be used. Higher pressure drops may be employed if the concomitant disadvantage of the higher inlet pressure is considered to be acceptable.

The organic amines used as starting materials may be any aliphatic, cycloaliphatic, aliphatic-aromatic or aromatic amines, diamines and/or polyamines. Suitable organic amines include, for example, aniline; halogen-substituted phenylamines such as 4-chlorophenylamine; 1,6-diaminohexane; 1-amino-3,3,5-trimethyl-5-aminomethylcyclohexane; 2,4-diaminotoluene and commercial mixtures thereof with 2,6-diaminotoluene, which generally contain up to 35% by weight of 2,6- diaminotoluene, based on the mixture; and polyamine mixtures of the diphenyl methane series which are obtainable by the known process of aniline/formaldehyde condensation. The amines mentioned in U.S. Pat. No. 3,321,283, column 4, lines 19 to 61, for example, may also be used.

The amines to be phosgenated may be introduced into the process according to the invention in a solvent-free form or as a solution in a substantially inert solvent at any suitable concentration. A high amine concentration saves energy for solvent recovery but may cause slight reduction in yield. The advantages and disadvantages related to solvent must be weighed against each other. The amines are frequently used at concentrations of from 5 to 50% by weight (preferably 5 to 40% by weight and most preferably 10 to 25% by weight) in the form of solutions in inert solvents. Preferred solvents include chlorinated aromatic hydrocarbons such as, for example, chlorobenzene, o-dichlorobenzene, p-dichlorobenzene, trichlorobenzenes, as well as the corresponding chlorotoluenes and chloroxylenes, chloroethylbenzene, monochlorobiphenyl, $\alpha$- and $\beta$-naphthylchloride, ethyl benzoate, dialkylphthalates, diethyl isophthalate, toluene, and xylenes. The solvents may be used singly or as mixtures. Other suitable solvents are described, for example, in U.S. Pat. No. 3,321,283, column 4, line 66, to column 5, line 2.

In the process according to the invention, phosgene is generally used in the form of 10 to 85% by weight (preferably 40 to 70% by weight, most preferably 40 to 65% by weight) solutions in inert solvents, preferably the same solvents as those used for the amine. The phosgene solutions may also contain recycling products of the process (mono- or polyisocyanate). If the phosgene solution contains any products of the process, phosgene must be present in large excess to prevent the formation of ureas by reaction of the primary amine with the isocyanate. That is, if the phosgene solutions contain mono- or polyisocyanates, the phosgene must always be present in at least a 2.5 times molar excess over the isocyanate groups in the solutions.

The equivalent ratio of phosgene to amine is generally at east 1.5:1, and in special cases may be up to 20:1, although the ratio is preferably in the range of 1.5:1 to 7:1, especially from 2:1 to 5:1.

The preparation of the reaction mixtures according to the invention using the mixing apparatus which are essential to this invention may, for example, be carried out as follows:

The temperature of the phosgene solution should be below the boiling point of the solution. Thus, cooled phosgene solutions are generally used. The temperature of the amine component generally depends on the physical properties of the amine (i.e., the melting point of the amine or the crystallization point of the amine solution used) and may vary within a wide range.

The solution forming the stream of larger volume is preferably passed through the constriction. If approximately equal volume streams are used, then either of the two components may form the middle stream or the side stream. Following this preference ensures optimum mixing and hence a satisfactory progress of the reaction.

According to a particular procedure, a flow rate of from 1 to 10 m/sec is normally maintained in the constriction. However, higher flow rates may be maintained in the constriction, for example, up to 50 m/sec, if the concomitant disadvantage of the higher pump inlet pressure is accepted. Conversely, the preferred flow rate of 1 to 10 m/sec has, of course, the advantage that it enables the inlet pressure to be kept low. The flow velocity in the constriction is generally from 2 to 50 times (preferably from 2 to 10 times) the flow velocity in the inlet pipe leading to the constriction.

The length L of the constriction is generally chosen to be at least equal to and preferably at least about twice its diameter D. This design provides exceptionally intensive mixing and enables the flow to be adequately stabilized.

It is particularly advantageous to arrange for the length $L_1$ of the constriction of the axially directed flow (i.e., to the point where the flow encounters the partial streams of the second component) to be equal to 0.5 to 2 times the diameter D of the constriction.

According to another particular embodiment of the new process, the product stream resulting from the two reactant streams is subjected to a constant, permanent constriction having a length $L_2$ that is at least equal to the length of the path in which the initial reaction of the amine component is substantially completed. The length $L_2$ is generally at the most twice the diameter D. Larger dimensions for $L_2$ result in higher pressure drops without providing any advantage.

The dimensions described above ensure that essentially no caked deposits will form in the nozzle.

A particularly high yield may be obtained by maintaining a ratio of output of the axially supplied stream $\epsilon_A$ to the laterally supplied stream $\epsilon_S$ in the range of 0.01 to 3.0, as represented by the following equation:

$$\frac{\epsilon_A}{\epsilon_S} = \frac{\rho_A \cdot v_A \cdot v_A^2}{\rho_S \cdot v_S \cdot v_S^2} = 0.01 \text{ to } 3.0$$

(preferably from 0.01 to 1.0 and most preferably from 0.05 to 0.7), where $\rho$ denotes the density (expressed in kg/m$^3$)

$v$ denotes the volume stream (expressed in m$^3$/sec) and v denotes the flow velocity (expressed in m/sec) the subscript A in each case denoting the axially moving stream and the subscript S denoting the laterally supplied stream.

The high yield obtainable by this procedure also ensures a low energy requirement.

According to another particular method of carrying out the process, the flow cross section increases downstream of the constriction, thereby ensuring that no eddy currents or back flow can take place. It goes without saying that the increase in flow cross section ends at a maximum which corresponds to the diameter of an attached pipe. Avoiding back flow is particularly effective in avoiding blockages and caked deposits.

According to another variation of the process, the number i of bores for the partial streams introduced laterally is chosen to be $2 \leq i \leq m$ (preferably $6 \leq i \leq m$), where m is obtained using the equation $$\frac{\pi \cdot D}{m \cdot d} > 1.1 \text{ (preferably } > 1.5,$$

in particular $>2$), where D denotes the diameter of the constriction and d denotes the diameter of each bore.

This measure also has an advantageous effect on the mixing process and hence on the reaction, as well as avoiding the formation of caked deposits.

All the bores are preferably arranged in a common plane perpendicular to the constriction, although deviations of this arrangement are possible. With such an arrangement, the initial reaction can take place essentially only in this plane, which means that product that has already undergone reaction does not again encounter the second component. The yield is thereby increased and the risk of deposit formation reduced, thus providing more economical process.

Since the phosgene solution generally constitutes the larger volume stream, it is generally conducted through the constriction in accordance with the above description.

The following procedure illustrates a method for preparing the reaction mixtures using the mixing apparatus required for the invention:

The main stream is supplied to a nozzle (1) from a feed pipe (2) which changes abruptly at the cut-off edge (11) on the barrier surface (10) into a constriction (3) situated in the nozzle (1). The barrier surface (10) is preferably set at an angle $\beta$ of $90° \pm 45°$ with the direction of flow. It is clear that this angle corresponds to the angle of the cut-off edge (11). The constriction (3) is arranged in an insert (4) and has a constant diameter D over its whole length L. At a distance $L_1$ equal, for example, to 1.5 times the diameter D of the constriction (3), a number of bores (5) (e.g., six) are evenly distributed over the circumference. Bores (5), which are situated substantially opposite one another, are offset by an amount equal to the diameter d so that the partial streams injected from them shoot through and past one another. The second component is delivered from a feed pipe (6) into a chamber (7) which surrounds the constriction (3) and from which the bores (5) extend. The length $L_2$ of the constriction (3) behind the bores (5) is equal, for example, to the diameter D of the constriction (3) and therefore covers approximately the region in which the initial reaction of the amine component is substantially completed. Behind the constriction (3), the nozzle (1) has a portion (8) of continuously increasing width so that it makes an angle $\alpha$ with the axis amounting to, e.g., 20°. This expanding portion (8) is followed by a discharge pipe (9) of the same diameter as the feed pipe (2).

The reaction mixtures which have been prepared in the mixing apparatus which is essential to this invention may subsequently be introduced into conventional reactors such as stirrer tanks or phosgenating towers to finish their reaction to produce the mono- or polyisocyanate end product. The chemical reaction resulting in the end product of the process is generally carried out in the temperature range of from 20 to 180° C.

In a particularly preferred embodiment of the process according to the invention, the reaction mixture which has been prepared in the mixing apparatus required for the invention is passed upwards from below through a reaction column containing perforated plates which subdivide the interior of the column into at least 10 (preferably 20 to 50) chambers which are separated from one another by these horizontal plates. It would be possible in principle but is by no means preferred to use several columns with perforated plates connected in series containing a total of 10 or more (preferably 20 to 50) chambers. Subdivision into a larger number of chambers provides no advantage, first, because a cushion of gas develops beneath each perforated plate which by its presence reduces the volume of reaction chamber available to the solid and liquid components of the reaction mixture and, second, because the additional improvement in the residence time distribution is minimal.

The perforations in the plates generally have a diameter of not more than 20 mm (preferably 2 to 10 mm). The preferred number of perforations is chosen according to the rate of throughput so that back mixing of the ascending reaction mixture between the individual chambers is largely prevented.

The reaction mixture ascending through the columns is a mixture of liquid components (solutions of the starting materials and of the isocyanates in the process of formation), gaseous components (phosgene and the hydrogen chloride formed in the process), and at least at the beginning of the reaction, solid components (carbamoyl chlorides or amine hydrochlorides suspended in the solvent). Reaction conditions are optimal when the velocity of the ascending gaseous phase is 2 to 20 m/sec (preferably 3.5 to 10 m/sec) in the perforations of the plates and the velocity of the ascending liquid phase is 0.05 to 0.4 g m/sec (preferably 0.1 to 0.2 m/sec) in the perforations of the plates.

In the preferred procedure using a column with perforated plates, the temperature of the reaction mixture leaving the mixing apparatus is generally from 40° to 100° C., whereas the temperature at the head of the reaction column is below 150° C., preferably from 70 to 130° C. and more preferably from 90° to 125° C. These temperatures are generally achieved by suitably heating the reaction column. To minimize the volume of the reaction apparatus required, it is advantageous to introduce the heat required for obtaining the desired overflow temperature in the lower region of the phosgenating tower or even before entry into the reactor. The arrangement prevents part of the volume of the reactor being ineffective due to its temperature being too low and therefore the overall reaction velocity also being too low.

The dimensions of the reaction column and the construction of the partitioning plates and the quantity of reaction mixture introduced into the column from below are generally designed to give an average residence time of the reaction mixture in the reaction column of at the most 120 minutes, preferably not more than 60 minutes.

The pressure at the head of the reaction column is generally from 1.2 to 3 bar (abs.) (preferably from 1.5 to 2.5 bar (abs.)), although higher or lower pressures may also be employed.

The reaction mixture leaving the top end of the reaction column and containing liquid and gaseous components is first freed from gaseous components (i.e., excess phosgene and hydrogen chloride) by any of several methods known in the art and then worked up by distillation. When the above-mentioned conventional reaction vessels are used for carrying out the phosgenating reaction, the chemical reaction is, of course, also followed by a distillative work-up of the reaction mixture. Before this distillation is carried out, however, fresh phosgene solution may be added to a part of the reaction mixture that is present as a solution and the enriched solution then returned to the beginning of the process.

The present invention, which is set forth in the foregoing disclosure, is not to be construed or limited either in spirit or in scope by these examples. Those skilled in the art will readily understand that known variations of the conditions and processes of the following preparative procedures can be used. In the following examples, all percentages are percentages by weight and all temperatures are degrees Celsius unless otherwise noted.

DESCRIPTION OF THE PREFERRED EMBODIMENTS

Annular perforated nozzles in which the constriction (3) is formed by an abrupt reduction in cross section of the feed pipe (2) and in which the barrier surface (10) forms an angle $\beta$ of 90° with the direction of flow are used in all the examples.

EXAMPLE 1

A solution of 550 kg/h of 3-chloro-4-methylphenylamine and 650 kg/h of monochlorobenzene ("MCB") was mixed with 3240 kg/h of a 50% solution of phosgene in MCB in an annular perforated nozzle having a constriction 14 mm in diameter D and 28 mm in length L ($L_1 = 18$ mm) with 10 bores 2.1 mm in diameter situated on the circumference of the constriction. The amine solution was introduced through the 10 lateral bores. The flow velocity of the phosgene solution in the constriction was 4.9 m/s and that of the amine solution in the lateral bores was 9.2 m/s. The output ratio of the two solutions, $\epsilon_A/\epsilon_S$, was 0.75. The reaction mixture was then phosgenated until clear at temperatures of 80°, 110° and 140° C., respectively, in a three-tank cascade in which each tank had a volume of 6 m³. The reaction product was worked up by distillation. Yield: 98.0%.

EXAMPLE 2

A solution of 450 kg/h of hexamethylene diamine (HDA) and 4050 kg/h of o-dichlorobenzene ("ODB") was mixed with 9000 kg/h of a 30% phosgene solution in ODB in an annular perforated nozzle having a constriction 19 mm in diameter D and 38 mm in length L ($L_1 = 28.5$ mm) with 12 bores 2.6 mm in diameter distributed over the circumference of the constriction. The amine solution was introduced through the 12 lateral bores. The flow velocity of the phosgene solution in the constriction was 6.5 m/s and that of the amine solution in the lateral bores was 16.4 m/s. The output ratio of the two solutions, $\epsilon_A/\epsilon_S$, was 0.32. The reaction mixture was then phosgenated until clear at temperatures of up to 150° C. in a reaction column of 17 m³ capacity containing 45 perforated plates. The reaction product was worked up by distillation. Yield: 96%.

EXAMPLE 3

A solution of 120 kg/h of trimethylhexamethylene diamine ("TMDA") and 145 kg/h of monochlorobenzene ("MCB") was mixed with 2835 kg/h of a 50% phosgene solution in MCB in an annular perforated nozzle having a constriction 10 mm in diameter D and 20 mm in length L ($L_1 = 15$ mm) with 4 bores 1.5 mm in diameter at the circumference of the constriction. The amine solution was introduced through the 4 lateral bores. The flow velocity of the phosgene solution in the constriction was 5.7 m/s and that of the amine solution in the lateral bores was 11.6 m/s. The output ratio of the two solutions, $\epsilon_A/\epsilon_S$, was 1.92. The reaction mixture was subsequently phosgenated until clear at temperatures of 80°, 110° and 140° C., respectively, in a three-tank cascade in which each tank had a volume of 6 m³. The reaction product was worked up by distillation. Yield: 94%.

EXAMPLE 4

A solution of 450 kg/h of 2,4-tolylene diamine ("TDA") and 2,360 kg/h of o-dichlorobenzene ("ODB") was mixed with 7,300 kg/h of a 50% phosgene solution in ODB in an annular perforated nozzle having a constriction 20 mm in diameter D and 36 mm in length L ($L_1 = 26$ mm) with 12 bores 2.6 mm in diameter situated at the circumference of the constriction. The amine solution was introduced through the 12 lateral bores. The flow velocity of the phosgene solution in the constriction was 4.8 m/s and that of the amine solution in the lateral bores was 10.3 m/s. The output ratio of the two solutions, $\epsilon_A/\epsilon_S$, was 0.55. The reaction mixture was then phosgenated until clear at temperatures of up to about 100° C. in a reaction column with a capacity of 7 m³ containing 23 perforated plates. The product was worked up by distillation. Yield: 96.7%.

EXAMPLE 5

A solution of 550 kg/h of a mixture of 65% of 2,4-tolylene diamine ("2,4-TDA") and 35% of 2,6-tolylene diamine ("2,6-TDA") and 2,500 kg/h of o-dichlorobenzene ("ODB") was mixed with 6,160 kg/h of a 58% solution of phosgene in ODB in an annular perforated nozzle having a constriction 20 mm in diameter D and 36 mm in length L ($L_1 = 26$ mm) with 12 bores 2.2 mm in diameter situated at the circumference of the constriction. The amine solution was introduced through the 12 lateral bores. The flow velocity of the phosgene solution in the constriction was 4.0 m/s and that of the amine solution in the 12 lateral bores was 15.7 m/s. The output ratio of the two solutions, $\epsilon_A/\epsilon_S$, was 0.13. The reaction mixture was subsequently phosgenated until clear at temperatures of up to about 100° C. in a reaction column equipped with 23 perforated plates. The product was worked up by distillation. Yield: 97%.

EXAMPLE 6

A solution of 1000 kg/h of a polyamine mixture of the diphenyl methane series ("MDA", dinuclear component about 65%, viscosity of 55 cP at 80° C.) and 4000 kg/h of o-dichlorobenzene ("ODB") was mixed with 7,140 kg/h of a 45% phosgene solution in ODB in an annular perforated nozzle having a constriction 23 mm in diameter D and 40.2 mm in length L ($L_1 = 30$ mm) with 12 bores 3.7 mm in diameter situated at the circumference of the constriction. The amine solution was introduced through the 12 lateral bores. The flow velocity of the phosgene solution in the constriction was 3.5 m/s and that of the amine solution in the 12 lateral bores was 9.2 m/s. The output ratio of the two solutions, $\epsilon_A/\epsilon_S$, was 0.20. The reaction mixture was phosgenated in two reaction columns arranged in series each of which contained 23 perforated plates and had an internal volume of 7 m³ and 3.5 m³, respectively, the phosgenation being carried out at temperatures of up to 85° C. in the first column and 155° C. in the second column. After removal of the solvent by distillation, the viscosity of the solvent free crude product was 45 mPa.s at 25° C. Yield: 100%.

What is claimed is:

1. A process for the continuous preparation of an organic monoisocyanate or polyisocyanate comprising
   a) mixing within a nozzle
   (i) a phosgene component comprised of a solution of phosgene in an organic solvent, and (ii) an amine component comprised of a monoamine or polyamine corresponding to the monoisocyanate or polyisocyanate, wherein said amine component is optionally dissolved in an organic solvent, by passing an axial stream of one said component (i) or (ii) through a constriction in said nozzle and introducing two or more lateral streams of the other said component (i) or (ii) into the axial stream through two or more lateral bores distributed over the circumference of the constriction in said nozzle, thereby forming a product stream; and b) allowing the components of the product stream to react.

2. A process according to claim 1 wherein the component having the larger volume stream is passed through the constriction as the axial stream.

3. A process according to claim 1 wherein the axial stream contains the phosgene component and the lateral streams contain the amine component.

4. A process according to claim 1 wherein a flow velocity of 1 to 10 m/sec is maintained in the constriction.

5. A process according to claim 1 wherein the constriction has a constant diameter over the entire length of said constriction.

6. A process according to claim 5 wherein the length of the constriction is equal to at least twice the diameter of said constriction.

7. A process according to claim 5 wherein the length of that part of the constriction through which the axial stream passes before mixing with the lateral streams is 0.5 to 2 times the diameter of said constriction.

8. A process according to claim 5 wherein the length of that part of the constriction through which the product stream passes after the axial stream and the lateral streams are mixed is at least as long as the path in which the initial reaction of the amine component is substantially completed.

9. A process according to claim 1 wherein the number of bores, i, for the lateral streams is chosen so that $2 \leq i \leq m$, wherein m is obtained using the formula $$\frac{\pi \cdot D}{m \cdot d} > 1.1,$$

wherein

D is the diameter of the constriction, and
d is the diameter of each bore.

10. A process according to claim 1 wherein the output ratio, $\epsilon_A/\epsilon_S$, of the axial stream to the sum of the lateral streams is 0.01 to 1.0, wherein $$\frac{\epsilon_A}{\epsilon_S} = \frac{\rho_A \cdot v_A \cdot v_A^2}{\rho_S \cdot v_S \cdot v_S^2},$$

wherein $\rho$ represents density,
$v$ represents stream volume,
$v$ represents flow velocity,
A denotes the axial stream, and
S denotes the lateral streams.

11. A process according to claim 1 wherein a) the axial stream contains the phosgene component and the lateral streams contain the amine component;

b) a flow velocity of 1 to 10 m/sec is maintained in the constriction;

c) the diameter of the constriction is constant over the entire length of said constriction;

d) the length of the constriction is equal to at least twice the diameter of said constriction;

e) the length of that part of the constriction through which the axial stream passes before mixing with the lateral streams is 0.5 to 2 times the diameter of the constriction;

f) the length of that part of the constriction through which the product stream passes after the axial stream and the lateral streams are mixed is at least as long as the path in which the initial reaction of the amine component is substantially completed;

g) the number of bores, i, for the lateral streams is chosen so that $2 \leq i \leq m$, wherein m is obtained using the formula $$\frac{\pi \cdot D}{m \cdot d} > 1.1,$$

wherein

D is the diameter of the constriction, and
d is the diameter of each bore; and h) the output ratio, $\epsilon_A/\epsilon_S$, of the axial stream to the sum of the lateral streams is 0.01 to 1.0, wherein $$\frac{\epsilon_A}{\epsilon_S} = \frac{\rho_A \cdot v_A \cdot v_A^2}{\rho_S \cdot v_S \cdot v_S^2},$$

wherein $\rho$ represents density,
$v$ represents stream volume,
$v$ represents flow velocity,
A denotes the axial stream, and
S denotes the lateral streams.

12. A process according to claim 1 wherein the flow cross section increases downstream of the constriction.

13. A process according to claim 1 wherein the product stream is worked up by distillation.

14. A process according to claim 11 wherein the product stream is worked up by distillation.

15. A process according to claim 1 wherein the product stream is continuously passed upwards from below at temperatures of up to 150° C. through a reaction column having at least 10 chambers separated by perforated plates.

16. A process according to claim 15 wherein the product stream is comprised of a gaseous phase and a liquid phase.

17. A process according to claim 16 wherein the gaseous phase has a velocity in the perforations of said perforated plates of 2 to 20 m/sec and the liquid phase has a velocity in the perforations of said perforated plates of from 0.05 to 0.4 m/sec.

18. A process according to claim 11 wherein the product stream is continuously passed upwards from below at temperatures of up to 150° C. through a reaction column having at least 10 chambers separated by perforated plates.

19. A process according to claim 18 wherein the product stream is comprised of a gaseous phase and a liquid phase.

20. A process according to claim 19 wherein the gaseous phase has a velocity in the perforations of said perforated plates of 2 to 20 m/sec and the liquid phase has a velocity in the perforations of said perforated plates of from 0.05 to 0.4 m/sec.

* * * * *